United States Patent [19]

Sunkara et al.

[11] Patent Number: 5,190,957
[45] Date of Patent: Mar. 2, 1993

[54] TREATMENT OF MULTI-DRUG RESISTANT TUMORS WITH QUINOLYL-AND ISOQUINOLYLOXAZOLE-2-ONES

[75] Inventors: Sai P. Sunkara; Winton D. Jones, both of Cincinnati, Ohio

[73] Assignee: Merrell Dow Pharmaceuticals Inc., Cincinnati, Ohio

[21] Appl. No.: 852,922

[22] Filed: Mar. 13, 1992

Related U.S. Application Data

[63] Continuation-in-part of Ser. No. 590,521, Oct. 3, 1990, abandoned, which is a continuation-in-part of Ser. No. 436,262, Nov. 3, 1989, abandoned.

[51] Int. Cl.⁵ .............................................. A61K 31/47
[52] U.S. Cl. ................................... 514/314; 514/307
[58] Field of Search .......................................... 514/314

[56] References Cited

U.S. PATENT DOCUMENTS 4,886,811 12/1989 Jones et al. .......................... 514/314
4,990,519 2/1991 Jones et al. .......................... 514/314

Primary Examiner—Jerome D. Goldberg
Attorney, Agent, or Firm—Stephen L. Nesbitt

[57] ABSTRACT

This invention relates to quinolyloxazole-2-ones which are useful in the treatment of multi-drug resistant tumors. The quinoloyloxazole-2-ones act to prevent drug resistance and thus allow conventional chemotherapeutic agents to kill tumor cells as if drug resistance were not present.

2 Claims, No Drawings

TREATMENT OF MULTI-DRUG RESISTANT TUMORS WITH QUINOLYL-AND ISOQUINOLYLOXAZOLE-2-ONES

CROSS-REFERENCE TO RELATED APPLICATIONS

This is a continuation-in-part of application Ser. No. 07/590,521, filed Oct. 3, 1990 now which is a continuation in part of application Ser. No. 07/436,262, filed Nov. 13, 1989, now abandoned.

This invention relates to the use of certain quinolyl- and isoquinolyloxazole-2-ones in the treatment of multidrug resistant tumors.

BACKGROUND OF THE INVENTION

Effective tumor treatment is frequently thwarted by the lack of sensitivity of certain tumors to standard chemotherapeutic agents (intrinsic resistance) or by the ability of certain tumors to develop a lack of chemotherapeutic sensitivity during the course of treatment (acquired resistance) The cause of this phenomena has, at least in part, been demonstrated to result from the existance of an energy-dependent efflux pump which acts to remove the chemotherapeutic agent from the target cell.

The pump consists of P-glycoprotein found as a constituent of cell membrane, and it has been suggested that the normal function of P-glycoprotein is to remove toxins from within the cell. This theory is supported by the observation that P-glycoprotein is found as a cell membrane constitutent in cells such as liver, kidney, colon, and jejunum. It has been suggested that P-glycoprotein in the cell membrane of such normal tissues could act to remove toxins or to assist in the transport of nutrients and solutes and in secreting a variety of protein and steroid substances. Natural presence of P-glycoprotein in tumor cells derived from these tissues as well as its presence in tumor cells derived from other tissue types could explain, at least in part, resistance of various tumors to therapy with standard chemotheraputic agents.

The use of therapeutic agents which inactivate the P-glycoprotein pump would be invaluable in the treatment of multidrug-resistant tumors. Quinidine and reserpine as well as the calcium channel blockers verapamil and diltiazem have been reported to reverse drug resistance in multidrug-resistant tumors Such agents could function by, for example, interfering with transcription of the P-glycoprotein gene, blocking the drug binding site on the P-glycoprotein or by decoupling the energy dependent driving mechanism of the efflux pump.

Applicants have determined that certain quinolyl- and isoquinolyloxazole-2-ones having PKC inhibiting activity are useful in the treatment of multi-drug resistant tumors. The quinolyl- and isoquinolyloxazolone-2-ones of this invention act to reverse drug resistance and therby allow standard chemotherapeutic agents to exhibit normal toxicity on tumors.

SUMMARY OF THE INVENTION

The present invention is directed to the use of certain quinolyl- and isoquinolyloxazole-2-ones of the formula

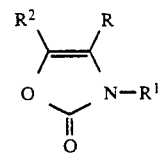

wherein
R and $R^1$ are each independently selected from the group consisting of hydrogen, $C_1$–$C_6$ alkyl, and phenyl or $C_1$–$C_3$ alkylphenyl wherein the phenyl ring is optionally substituted with one, two or three of the substituents selected from the group consisting of fluorine, chlorine, bromine, $C_1$–$C_4$ alkyl, and $C_1$–$C_4$ alkoxy; and
$R_2$ is a 2-, 3-, or 4-quinolyl group or a 1, 3-, or 4isoquinolyl group wherein the quinolyl or isoquinolyl group is optionally substituted with one, two or three of the substituents selected from the group consisting of fluorine, chlorine, bromine, $C_1$–$C_4$ alkyl, $C_1$–$C_4$ alkoxy, nitro, trifluoromethyl, or phenyl wherein the phenyl is optionally substituted by a member of the group consisting of fluorine, chlorine, bromine, $C_1$–$C_4$ alkyl, and $C_1$–$C_4$ alkoxy; or $R_2$ is a 5-, 6-, 7-, or 8-quinolyl or isoquinolyl group;
and the pharmaceutically-acceptable salts thereof in the treatment of multidrug-resistant tumors.

DETAILED DESCRIPTION OF THE INVENTION

This invention concerns the use of the compounds of Formula I as agents effective in the treatment of multidrug resistant tumors. Specifically the compounds of formula I, when administered together with standard chemotherapeutic agents, can be used in the treatment of tumors which are intrinsically or extrinsically drug resistant.

As used herein, the terms "$C_1$–$C_3$ alkyl", "$C_1$–$C_4$ allyl" and "$C_1$–$C_6$ alkyl" mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propynyl, butenyl, butadienyl, isopropenyl, and the like. The term "$C_1$–$C_4$ alkoxy" means alkoxy groups having from one to four carbon atoms, and includes such groups as methoxy, ethoxy, n-propoxy, isopropoxy, n-butoxy, isobutoxy, sec-butoxy, tert-butoxy, and the like. When R or $R^1$ is "optionally substituted phenyl or $C_1$–$C_3$ alkylphenyl", the one, two or three substituent(s) can be located at any available position on the phenyl ring. When $R^2$ is 2-, 3-, or 4-quinolyl or 1-, 3-, or 4isoquinolyl the optional substituent(s) can be located at any available position(s) on the quinolyl or isoquinolyl ring.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of this invention include compounds of Formula I wherein the R groups are designated as follows:

| R | $R^1$ | $R^2$ |
|---|---|---|
| hydrogen | hydrogen | 2-, 3-, or 4-quinolyl |
| ethyl | hydrogen | 2-, 3-, or 4-quinolyl |
| propyl | hydrogen | 5-, 6-, 7-, or 8-quinolyl |
| methyl | benzyl | 2-, 3-, or 4-quinolyl |
| phenethyl | hydrogen | 2-, 3-, or 4-quinolyl |
| propyl | hydrogen | 2-, 3-, or 4-(6,7-dimethyl)-quinolyl |
| propyl | hydrogen | 2-, 3-, or 4-(6-phenyl)-quinolyl |
| 4-methoxyphenethyl | hydrogen | 2, 3-, or 4-quinolyl |
| benzyl | benzyl | 2-, 3-, or 4-(7-ethoxy)-quinolyl |
| benzyl | benzyl | 2-, 3-, or 4-(7-phenyl)-quinolyl |
| butyl | hydrogen | 2-, 3-, or 4-quinolyl |
| 3,5-dichloro)phenylpropyl | methyl | 5-, 6-, 7-, or 8-quinolyl |
| propyl | methyl | 2-, 3-, or 4-quinolyl |
| 3,5-dimethoxybenzyl | ethyl | 5-, 6-, 7-, or 8 quinolyl |
| methyl | propyl | 2-, 3-, or 4-(5-ethoxy-7-methyl)-quinolyl |
| methyl | propyl | 2-, 3-, or 4-(5-phenyl)-quinolyl |
| butyl | butyl | 5-, 6-, 7-, or 8-quinolyl |
| hydrogen | phenethyl | 2-, 3-, or 4-(6-trifluoromethyl)-quinolyl |
| hydrogen | phenethyl | 2-, 3-, or 4-(6-phenyl)-quinolyl |
| methyl | 4-methoxy-phenethyl | 2-, 3-, or 4-quinolyl |

Equivalently substituted isoquinolyl derivatives are also intended. As is true for most classes of therapeutically effective compounds, certain subclasses and certain species which are especially effective are preferred over others. In this instance, those compounds of Formula I wherein $R^2$ is optionally substituted 2-, 3-, or 4-quinolyl are preferred. Also preferred are compounds wherein R is $C_1-C_6$ alkyl, as well as compounds wherein $R^2$ is an unsubstituted 2-, 3-, or 4-quinolyl group, R is ethyl or propyl and $R^1$ is hydrogen.

The 2-, 3-, or 4-quinolyloxazole-2-ones of this invention can readily be prepared by the reaction depicted in Reaction Scheme 1.

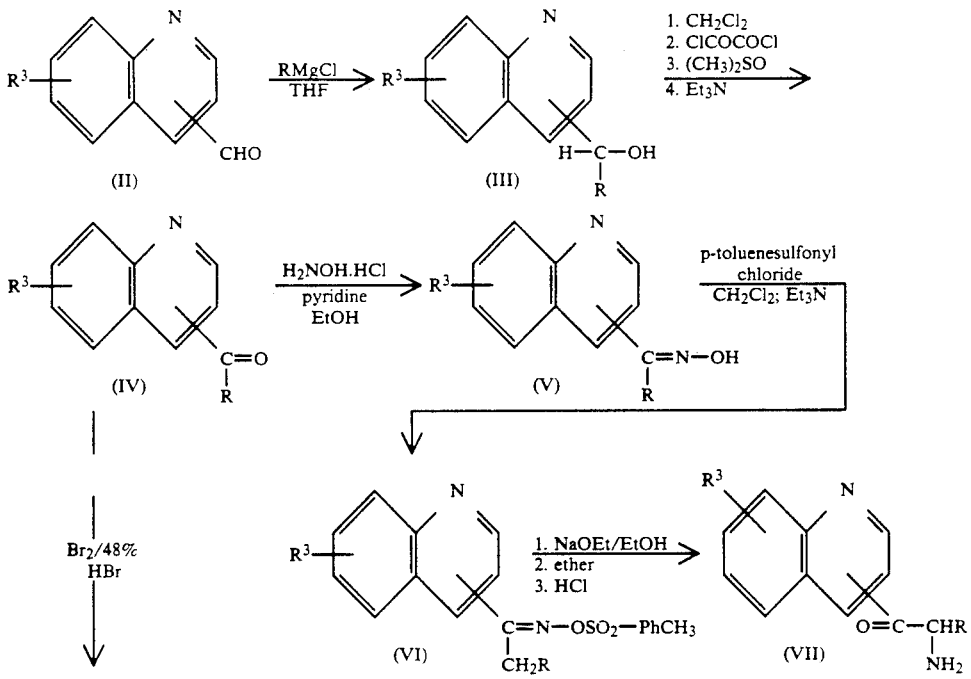

Reaction Scheme 1

-continued

Reaction Scheme 1

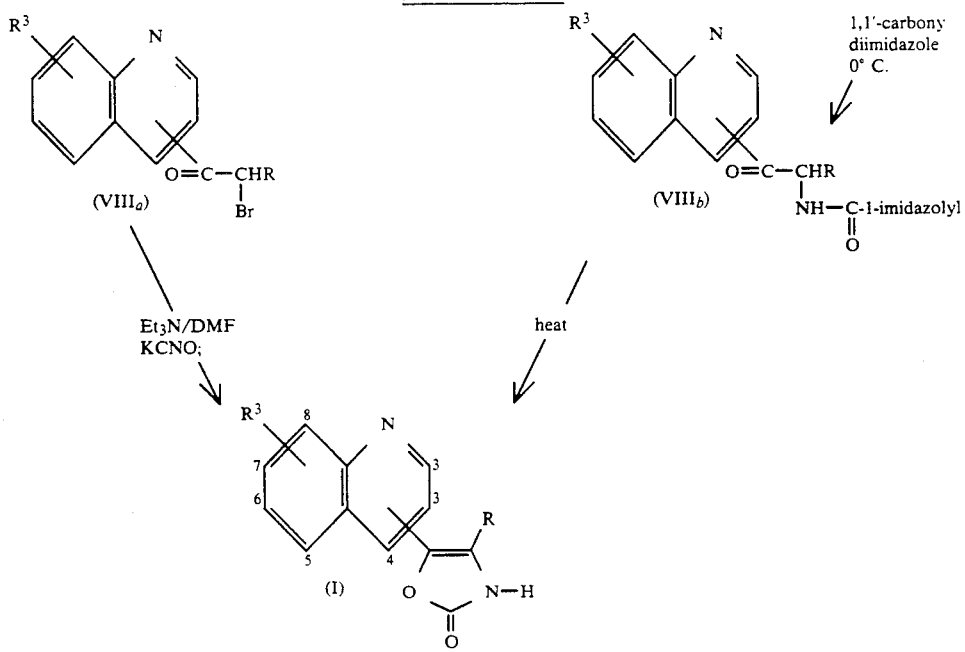

wherein R is as in Formula I, R3 is the optional R² group substituent(s) of Formula I, and other symbols are as defined hereinafter.

In essence, Reaction Scheme 1 illustrates that the 2-, 3-, or 4-quinolyloxazole-2-ones of Formula I can be prepared by reacting the appropriate and readily available 2-, 3-, or 4-quinoline carboxaldehyde (II) in tetrahydrofuran (THF) with alkylmagnesium chloride or with optionally substituted phenylalkyl-magnesium chloride [RMgCl] to produce 2-, 3-, or 4-quinoline alkanol (III), which is in turn oxidized with oxalyl chloride (ClCOCOCl), methyl sulfoxide [(CH₃)₂SO] and triethylamine (Et₃N) in dichloromethane (CH₂Cl₂) to produce quinolyl-alkanone (IV). The alkanone (IV) can alternately be brominated to compound (VIIIa) and further treated with triethylamine in dimethylformamide (DMF) in the presence of potassium cyanate (KCNO) to form the compounds of Formula I according to procedures well known in the art and illustrated in the examples herein; or compound IV can be converted to oxime (V) by refluxing with hydroxylamine hydrochloride (H₂NOH.HCl) and pyridine in ethanol (EtOH). Compound (V) is then reacted with p-toluenesulfonyl chloride and triethylamine in dichloromethane to produce compound (VI). The amine (VII) is then produced by reacting compound (VI) with sodium ethoxide in ethanol (NaOEt/EtOH), followed by ether and aqueous hydrochloric acid HCl) extraction. The amine (VII) is further reacted with 1,1'-carbonyldiimidazole at about 0° C. to form compound (VIIIb), which is then heated to about 170° C. to yield the appropriate 2-, 3-, or 4-quinolyloxazole-2-ones of Formula I. The unsubstituted 5-, 6-, 7- or 8-quinolyloxazole-2-ones of this invention can readily be prepared by the reaction depicted in Reaction Scheme 2.wherein R is as in Formula I, R³ is the optional R² group substituent of Formula I, and other symbols are as defined for Reaction Scheme 1.

Thus unsubstituted 5-, 6-, 7- or 8-quinolyloxazole-2-ones of this invention can readily be prepared by the reaction depicted in Reaction Scheme 2.

Reaction Scheme 2

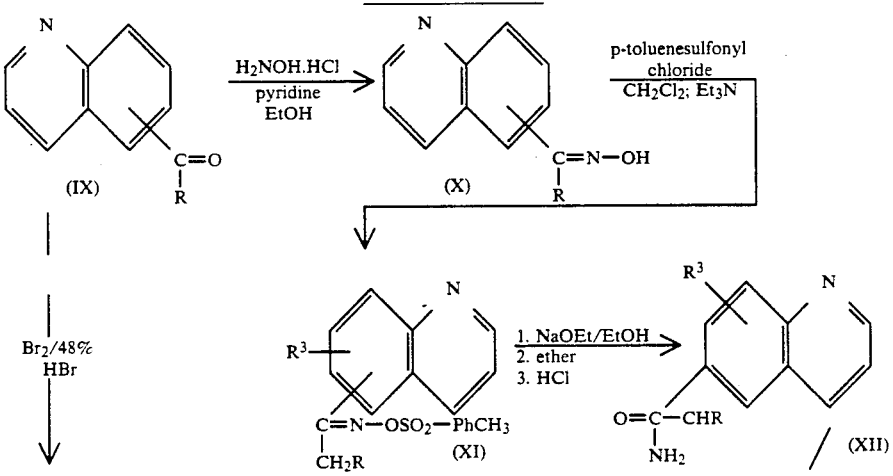

Reaction Scheme 2

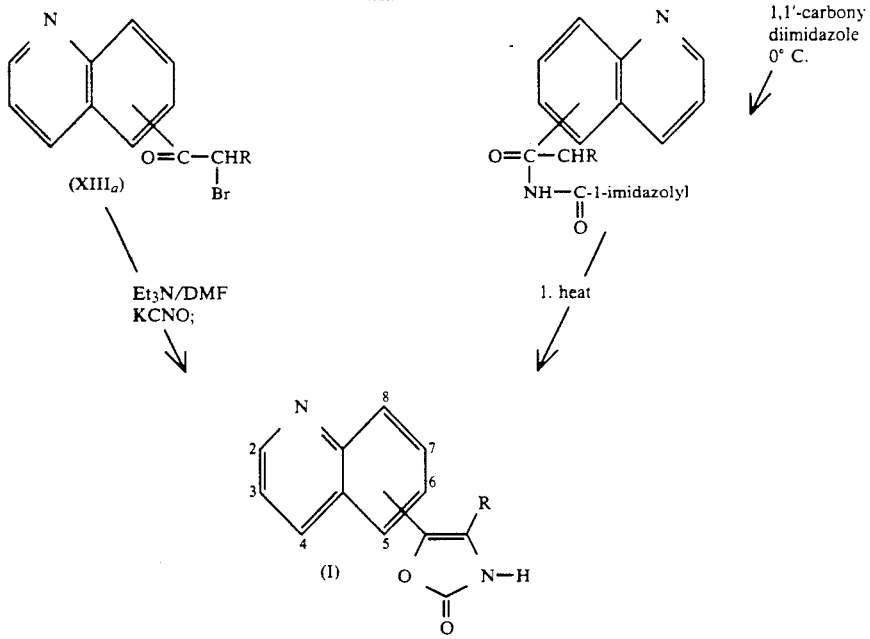

wherein R is as in Formula I, $R^3$ is the optional $R^2$ group substituent of Formula I, and other symbols are as defined for Reaction Scheme 1.

In essence, Reaction Scheme 2 illustrates that the 5-, 6-, 7-, or 8-quinolyloxazole-2-ones of Formula I can be prepared in essentially the same manner as described for Reaction Scheme 1. The alkanone starting material (IX) is prepared by metalating 5-, 6-, 7- or 8-bromoquinoline according to a procedure by H. Gilman and T. Suddy set forth in *J. Org. Chem.* 23, 1584-9 (1958), and then reacting it with N-alkoxy-N-alkylamine. The 5-, 6-, 7-, or 8-bromoquinoline compounds are prepared by following procedures set forth in "The Chemistry of Heterocyclic Compounds" by Gurnos Jones, as found in *Quinolines*, Part 1, vol. 32, p. 100-117 and 247-258, ed. A. Weissberger and E. C. Taylor, John Wiley and Sons, London, 1977. These procedures can also be utilized for preparing 2-,3-, or 4-bromoquinolines and their corresponding 2-, 3-, or 4-quinolinyl alkanones such as those of formula (IV) in Reaction Scheme 1.

Alternatively, the formula (IV) and formula (IX) compounds of Reaction Schemes 1 or 2 can also be prepared by reacting the appropriate bromoquinoline with butyl lithium in an appropriate solvent such as THF or diethyl ether at −70° C. to 0° C., preferably at −50° C., and then reacting the lithiated compound with

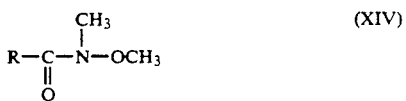

(XIV)

wherein R is as described in Formula I. This reaction is further specifically exemplified in Example 8. Compound (XIV) can be prepared by a procedure set forth in *Tetrahedron Letters*, 22, 3815 (1981).

The compounds wherein $R^1$ is $C_1$-$C_6$ alkyl or optionally substituted $C_1$-$C_3$ alkylphenyl are produced by subsequent reaction of the compound of Formula I of either Reaction Scheme 1 or Reaction Scheme 2 with sodium hydride and the appropriate alkyl iodide or phenylalkyl iodide in tetrahydrofuran according to procedures well known in the art.

Likewise, one of ordinary skill will readily be able to modify these procedures to obtain isoquinoline derivatives of formula 1.

The ability of the oxazolone derivatives of this invention to reverse drug resistance in multi-drug resistant tumors can be demonstrated by the ability of test compounds to reduce acell growth in vinblastine (VBL) resistant tumor cell line.

$CHO^R$ cells were plated at a density of 1X105/35mm dish and were allowed to grow overight at 37° C. in a $CO_2$ incubator. The medium was replaced with medium containing the compounds and vinblastine (0.2 μg/ml). The cells were allowed to grow for further 72 hr and the cell number was determined by Coulter counter after trypsiunization. VLB alone at 0.2 μg/ml did not have any effect on cell growth. The results of such a study employing 4-propyl-5-(4-quinolinyl)-2(3H)-oxozolone is tabulated in Table 1.

TABLE 1

REVERSAL OF MULTIDRUG RESISTANCE (MDR) IN CHO ® CELLS BY 4-PROPYL-5-(4-QUINOLINYL)-2(3H)-OXAZOLONE

| Concentration | % Inhibition of Cell Growth | |
| --- | --- | --- |
| (μg/ml) | Compound Only | Compound + VLB |
| 10 | 14 | 93 |
| 5 | 0 | 93 |
| 1 | 0 | 43 |
| 0.1 | 0 | 4 |

The term "patient" used herein is taken to mean mammals such as primates, including humans, sheep, horses, cattle, pigs, dogs, cats, rats and mice.

The amount of the oxazoline derivative of formula 1 to be administered can vary widely according to the particular dosage unit employed, the period of treatment, the age and sex of the patient treated, the nature and extent of the drug resistance in the tumor to be treated, and the particular oxazolone derivative selected. The oxazolone derivative is used in conjunction with other chemotherapeutic agents known to be useful in the treatment of tumors. The amount of a oxazolone derivative of formula 1 effective to reverse drug resistance will generally range from about 15 mg/kg to 500 mg/kg. A unit dosage may contain from 25 to 500 mg of the oxazolone derivative, and can be taken one or more times per day. The oxazolone derivative can be administered with a pharmaceutical carrier using conventional dosage unit forms either orally or parenterally.

Treatment of tumors by the method of this invention requires that an anti-tumor effective amount of a chemotherapeutic agent be administered together with a compound of formula 1. Tumors which can be treated by the method of this invention include both benign and malignant tumors or neoplasms, and include melanomas, lymphomas, leukemias, and sarcomas. Illustrative examples of tumors are cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseus or non-osseus sarcomas, breast tumors; tumors of the pituitary, thyroid and adrenal cortex; gastrointestinal tumors, such as those of the esophagus, stomach, intestine and colon; pancreatic and hepatic tumors; laryngeae papillomestasas and lung tumors. Of course those tumors which typically are or become multi-drug resistant are most beneficially treated with the method of this invention. Such tumors include colon tumors, lung tumors, stomach tumors, and liver tumors. The effective amount of chemotherapeutic agent used in the method of this invention varies widely and depends on factors such as the patient, the tumor tissue type and its size, and the particular chemotherapeutic agent selected. The amount is any effective amount and can be readily determined by those skilled in the art. In general, less chemotherpeutic agent will be required when administered with the oxazolones of formula 1, primarily because the problem of drug resistance need not be addressed by the addition of larger quantities of chemotherapeutic agent. Of course mixtures of chemotherapeutic agents may be employed and surgical excission and radiation therapy may be useful adjuvents as in any tumor therapy. While the compound of formula 1 and the chemotherapeutic agent are said to be administered together, this does not necessarily mean that the compounds are formulated into the same dosage form or are administered concurrently. Rather, the expression "together" means that a compound of formula 1 and the chemotherapeutic agent(s) are administered in a combined dosage form or separately during the course of therapy.

The preferred route of administration is oral administration. For oral administration the oxazolone derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The oxazolone derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-betaaminopropionates, and 2-alkylimidazoline quarternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a nonionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The following specific examples are presented to illustrate the synthesis of the compounds of this invention, but they should not be construed as limiting the scope of this invention in any way.

EXAMPLE 1

1 Butyl 4-Quinoline methanol (III)

In a 1 liter, 3-necked flask equipped with a mechanical stirrer, dropping funnel, reflux condenser (all dried under argon), and thermometer, were placed 15.0 grams (0.0954 M) of 4-quinoline carboxaldehyde and 400 ml of dry tetrahydrofuran (THF). The mixture was cooled by means of stirring in a dry ice/methanol bath to $-70°$ C. Butylmagnesium chloride (100 ml of 2 M) was added through the funnel at a fast drop rate over a period of about 45 minutes, and the mixture was allowed to stir at $-70°$ C. for about an hour. Then, 100 ml saturated ammonium chloride ($NH_4Cl$) was added dropwise through the funnel and the mixture was allowed to warm to room temperature whereupon the resulting semi-solid material was filtered off under vacuum and washed with about 100 ml THF. The THF layers were combined and washed with saturated sodium chloride solution and then dried over magnesium sulfate. The inorganic matter was filtered off by vacuum through diatomaceous earth and the solvent evaporated. The residue was flash chromatographed on silica (1:1 ethyl acetate/hexane) and, after evaporation of the solvent, about 5.0 gram of purified title compound was recovered.

EXAMPLE 2

1-(4-Quinolinyl)-1-Pentanone (IV)

In a 1 liter, 3-necked flask equipped with a mechanical stirrer, dropping funnel, reflux condenser (all dried under argon), and thermometer, were placed 50 ml of dry dichloromethane and 3.79 ml (0.043 M) oxalyl chloride. The resulting mixture was stirred in a dry ice/methanol bath to maintain a temperature of $-70°$ C. Methyl sulfoxide (6.17 ml, 0.043 M) was added dropwise and subsequently a solution of 9.26 grams (0.043 M) of the compound of Example 1 in dry dichloromethane ($CH_2Cl_2$) was added and the mixture allowed to stir cold for about 15 minutes. Triethylamine (35.6 ml) was then added and the mixture was allowed to stir cold for about 1 hour. After the mixture had been allowed to warm to room temperature, it was poured into a flask containing about 600 ml water. The $CH_2Cl_2$ layer was separated and the aqueous layer extracted with $CH_2Cl_2$ (2 times, 100 ml each). The combined $CH_2Cl_2$ layers were washed with saturated sodium chloride and dried over magnesium sulfate. The inorganic matter was filtered off and the solvent evaporated leaving a residue that was flash chromatographed as in Example 1. Evaporation left 9.0 grams of title compound.

EXAMPLE 3

1-(4-Quinolinyl)-1-Pentanone Oxime (V)

In a 500 ml, 3-necked flask equipped with a mechanical stirrer, dropping funnel, reflux condenser (all dried under argon), were placed 8.3 grams (0.03892 M) of the compound of Example 2, 4.12 grams (0.0584 M) of hydroxylamine hydrochloride, 40 ml of dry pyridine, and about 200 ml of dry ethanol The mixture was refluxed for 6 hours, then the solvent was evaporated leaving a residue which was treated with about 400 ml ether and 200 ml water. The ether layer was separated and washed several times with water, washed with saturated sodium chloride and dried over magnesium sulfate. The inorganic matter was filtered off and the solvent evaporated, leaving 8.42 grams (94.7%) of the title compound.

EXAMPLE 4

1 (4-Quinolinyl)-1-Pentanone-0-[(4-Methylphenyl)Sulfonyl] Oxime (VI)

In a 250 ml erhlenmeyer flask filled with argon were placed 8.42 grams (0.0369 M) of the compound of Example 3 and about 130 ml dry $CH_2Cl_2$. While stirring and cooling to about 0° C. in an ice/methanol bath, about 20 ml of triethylamine was added over a 5 minute period, then 10.55 grams (0.0554 M) toluenesulfonyl chloride was added and the mixture allowed to stir for 3 hours. The solution was then evaporated to dryness which left a residue that was treated with ether and water. The ether phase was separated and the water phase extracted twice more with ether. The combined ether layers were extracted with dilute sodium hydroxide, washed with saturated sodium chloride and dried over magnesium sulfate. The inorganic matter was filtered off using vacuum, and the solvent was evaporated leaving 15.1 grams of the title compound.

EXAMPLE 5

2-Amino-1 (4-Quinolinyl)-1 Pentanone (VII)

In a 250 ml, 3-necked flask equipped with a mechanical stirrer, dropping funnel, reflux condenser (all dried under argon), was placed 60 ml dry ethanol. While stirring, 2.55 grams (0.111 M) of sodium spheres were added and allowed to continue to stir under argon until the sodium dissolved. A solution of 15.1 grams of the compound of Example 4 in ethanol was then added and the mixture stirred for 4 hours at room temperature. The mixture was then poured into a flask containing 1200 ml absolute ether. The resulting precipitate was filtered off under vacuum through diatomaceous earth, and the filtrate extracted with 2N hydrochloric acid (3 times, 170 ml each). The extract was evaporated leaving 19.8 grams of the title compound.

EXAMPLE 6

N-[2-Oxo-1-Propyl-2-(4-Quinolinyl)Ethyl]-1H-Imidazole-1-Carboxamide ($VIII_b$)

The compound of Example 5 (19.8 grams) was dissolved in about 300 ml water, and the solution filtered by gravity into a 1 liter, 3-necked flask equipped with a mechanical stirrer and a thermometer. The solution was cooled to 0° C. with stirring in an ice/methanol bath, and 29.87 grams (0.185 M) 1,1'-carbonyldiimidazole was added over a 5 minute period. The mixture was allowed to stir cold for about 15 minutes. The resulting precipitate was taken up in about 500 ml ethyl acetate and separated from the water. The solution was washed with saturated sodium chloride and dried over magnesium sulfate, and the inorganic matter filtered off using diatomaceous earth under vacuum. The solvent was evaporated leaving the title compound.

EXAMPLE 7

4-Propyl-5-(4-Quinolinyl)-1 (3H) Oxazolone (I)

The compound of Example 6 (12 grams) was heated under vacuum to 170° C. for about 30 minutes, allowed to cool to room temperature and washed with water. The water was decanted and the residue was treated with $CH_2Cl_2$ (20 ml). The $CH_2Cl_2$ was evaporated leaving 7.8 grams of residue. The product was purified by means of flash chromatography on silica, eluting with ethyl acetate. The solvent was evaporated and the residue dissolved in 48 ml hot 50% ethanol, filtered and allowed to cool to room temperature. The precipitate was collected by vacuum filtration and dried in vacuo at 78° C., leaving 1.97 grams (21%) title compound. M.p. 188°–190° C. dec.; analysis calced. for $C_{15}H_{14}N_2O_2$: C, 70.85; H, 5.55: N, 11.02; analysis found: C, 71.10: H, 5.73: N, 10.76.

EXAMPLE 8

1-(3-Quinolinyl)-1-butanone

In a dry 3-necked flask under argon at −50° C., n-butyl lithium (0.0025 M, 0.021 ml) was added to 150 ml diethylether. Then 4.16 grams 3-bromoquinoline in 2 ml THF was added dropwise while stirring and maintaining the temperature at −60° C. to −55° C. The solution was stirred for 30 minutes, and 2.3 grams N-methyl-methoxybutyramide were then added dropwise at −50° C. and the solution was stirred an additional 30 minutes. The solution was then allowed to warm to 0° C. and stirred for one hour. The reaction was quenched with a saturated solution of ammonium chloride and the THF layer separated, washed with brine, separated, and dried over magnesium sulfate. Filtration through diatomaceous earth, followed by concentration and subsequent thin layer chromatography (35% ethylacetate/65% $CH_2Cl_2$) gave a total yield of 2.03 g (51%) of the title compound.

By substituting the following starting materials for the 4-quinoline carboxaldehyde and/or the butylmagnesium chloride of Example 1, and following the procedures set forth in Examples 1 through 7, the following end products can be made in a like manner.

A. 6- or 8-methoxy-4-quinoline carboxaldehyde and methylmagnesium chloride, to yield 5-(6- or 8-methoxy-4-quinolinyl)-1-(3H)-oxazolone B. 2-quinololine carboxaldehyde and methylmagnesium chloride, to yield 5-(2-quinolinyl)-1-(3H)-oxazolone C 7- or 8-chloro-4-quinoline carboxaldehyde and propylmagnesium chloride, to yield 4-ethyl-5-(7- or 8-chloro-4-quinolinyl)-1-(3H)-oxazolone D. 6,8-dichloro or dibromo-4-quinoline carboxaldehyde and butylmagnesium chloride, to yield 4-propyl-5-(6,8-dichloro or dibromo-4-quinolinyl)-1-(3H)-oxazolone E. 7- or 8-nitro-4-quinoline carboxaldehyde and pentylmagnesium chloride, to yield 4-butyl-5-(7- or 8-nitro-4-quinolinyl)-1-(3H)-oxazolone F. 7-trifluoromethyl-4-quinoline carboxaldehyde and hexylmagnesium chloride, to yield 4-pentyl-5-(7-trifluoromethyl-4-quinolinyl)-1-(3H)-oxazolone G. 5,8-dimethoxy-4-quinoline carboxaldehyde and benzylmagnesium chloride, to yield 4-phenyl-5-(5,8-dimethoxy-4-quinolinyl)-1-(3H)-oxazolone H. 5,8-dimethoxy-6-nitro-4-quinoline carboxaldehyde and ethylmagnesium chloride, to yield 4-methyl-5-(5,8-dimethoxy-6-nitro-4-quinolinyl)-1-(3H)-oxazolone I. 6-methoxy-8-nitro-4-quinoline carboxaldehyde and propylmagnesium chloride, to yield 4-ethyl-5-(6-methoxy-8-nitro-4-quinolinyl)-1-(3H)-oxazolone J. 5,6-dimethoxy-8-nitro-4-quinoline carboxaldehyde and pentylmagnesium chloride, to yield 4-butyl-5-(5,6-dimethoxy-8-nitro-4-quinolinyl)-1-(3H)-oxazolone K. 5-methyl-4-quinoline carboxaldehyde and benzylmagnesium chloride, to yield 4-phenyl-5-(5-methyl-4-quinolinyl)-1-(3H)-oxazolone L. 2-(4-methoxy)phenyl-4-quinoline carboxaldehyde and 3,5-dimethoxybenzymagnesium chloride, to yield 4-(3,5-dimethoxyphenyl)-5-[1-(4-methoxyphenyl)-4-quinolinyl]-1(3H)-oxazolone M. 6,8-dimethoxy-4-quinoline carboxaldehyde and 4-methylbenzylmagnesium chloride, to yield 4-(4-methylphenyl)-5-(6,8-dimethoxy-4-quinolinyl)-1-(3H)-oxazolone N. 4-quinolinecarboxaldehyde and propylmagnesium chloride, to yield 4-ethyl-5-(4-quinolinyl)-1(3H)-oxazolone (mp 273°–76° C.)

O. 4-quinolinecarboxaldehyde and pentylmagnesium chloride, to yield 4-butyl-5-(4-quinolyl-1(3H)-oxazolone (mp 196°–98° C.)

P. 3-quinolinecarboxaldehyde and butylmagnesium chloride, to yield 4-propyl-5-(3-quinolyl)-1(3H)-oxazolone (mp 193°–95° C.)

Q. 4-isoquinolinecarboxaldehyde and butylmagnesium chloride to yield 4-propyl-5-(4-isoquinolyl)-1(3H)-oxazolone (mp 122°–24° C.).

By substituting 1-(3-quinolinyl)-1-pentanone for the compound of Example 2 and by following the procedure set forth in Examples 3 through 7, 4-propyl-5-(3-quinolinyl)-(3H)oxazolone is produced.

In a like manner, by substituting the following starting materials for 1-(4-quinolinyl)-1-pentanone of Example 2 and following the procedure set forth in the preceding paragraph, the following end products can be made.

R. 1-(5-quinolinyl)-1-pentanone, to yield 4-propyl-5-(5-quinolinyl)-1-(3H)-oxazolone S. 1-(6-quinolinyl)-1-butanone, to yield 4-ethyl-5-(6-quinolinyl)-1-(3H)-oxazolone T. 1-(7-quinolinyl)-1-ethanone, to yield 5-(7-quinolinyl)-1-(3H)-oxazolone U. 1-(8-quinolinyl)-1-phenylethanone, to yield 4-phenyl-5-(8-quinolinyl)-1-(3H)-oxazolone V. 1-(5,8-dimethoxy-3-quinolinyl)-1-propanone, to yield 4-methyl-5-(5,8-dimethoxy-3-quinolinyl)-1-(3H)-oxazolone.

The following specific examples are presented to illustrate compositions of this invention, but they should not be construed as limiting the scope of this invention in any way.

EXAMPLE 9

A tablet is prepared from

| | |
|---|---|
| 4-Methyl-5-(3-quinolinyl)-1-(3H)-oxazolone | 250 mg |
| Starch | 40 mg |
| Talc | 10 mg |
| Magnesium | 10 mg |

EXAMPLE 10

A capsule is prepared from

| | |
|---|---|
| 4-phenyl-5-(2-quinolinyl)-1-(3H)-oxazolone | 400 mg |
| Talc 40 mg | |
| Sodium Carboxymethy celulose | 40 mg |
| Starch | 120 mg |

It should be apparent to one of ordinary skill in the art that changes and modifications can be made to this invention without departing from the spirit or scope of the invention as it is set forth herein.

What is claimed is:

1. A method of reversing vinblastine resistance in a vinblastine resistant tumor by administering to a patient, in need thereof, an effective amount of a compound according to the formula:

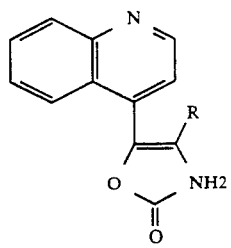

wherein R is selected from the group consisting of hydrogen and $C_1-C_6$ alkyl.

2. The method of claim 1 wherein R is propyl.